United States Patent [19]

Schanus et al.

[11] Patent Number: 5,286,630
[45] Date of Patent: Feb. 15, 1994

[54] YEAST EXTRACTS FROM CANDIDA UTILIS AND THE PRODUCTION OF SAME

[75] Inventors: Edward G. Schanus, Warrenton, Oreg.; Marinelle McPherson, Bartlesville, Okla.

[73] Assignee: Phillips Petroleum Company, Bartlesville, Okla.

[21] Appl. No.: 802,578

[22] Filed: Dec. 5, 1991

[51] Int. Cl.$^5$ .......................... C12P 1/02; A23L 1/28; A23L 2/26; A23J 1/00

[52] U.S. Cl. .................................. 435/41; 435/71.1; 435/171; 435/255.4; 426/60; 426/533; 426/656

[58] Field of Search ................ 435/41, 171, 256, 71.1, 435/255.4; 426/60, 533, 656

[56] References Cited

U.S. PATENT DOCUMENTS

| | | | |
|---|---|---|---|
| 3,867,555 | 2/1975 | Newell et al. | 426/60 |
| 3,887,431 | 6/1975 | Robbins et al. | 426/656 |
| 3,888,839 | 6/1975 | Newell et al. | 530/371 |
| 4,066,793 | 1/1978 | Eguchi | 426/60 |
| 4,135,000 | 1/1979 | Schuldt | 426/60 |
| 4,285,976 | 8/1981 | Akin et al. | 426/60 |
| 4,810,509 | 3/1989 | Kanegae et al. | 426/60 |

OTHER PUBLICATIONS

Economic Microbial "Fermented Foods"–vol. 7, 1982.
Process Biochemistry, May 1970, pp. 50–52.
Prepared Foods, Jan. 1988, p. 150.
Prepared Foods, Apr. 1987, p. 148.
Agric. Biol. Chem. 52 (10) pp. 2679–2681 (1988).

*Primary Examiner*—Marian Knode
*Attorney, Agent, or Firm*—Marianne H. Michel; Cynthia L. Stokes

[57] ABSTRACT

Yeast extracts from *Candida utilis* which can be used as flavor enhancers and emulsifiers are disclosed. One flavor enhancing extract and one emulsifying extract is derived from raw *Candida utilis*; one flavor enhancing extract and one emulsifying extract is derived from pasteurized *Candida utilis*.

5 Claims, No Drawings

YEAST EXTRACTS FROM CANDIDA UTILIS AND THE PRODUCTION OF SAME

The present invention relates to novel yeast extracts which exhibit flavor enhancing properties and emulsifying properties and which are derived from *Candida utilis*.

BACKGROUND

Various forms of yeast protein have served as the means for providing flavor enhancement, especially for beef and poultry.

Yeast extract consists of the protein and other intracellular material extracted from yeast cells by a process known as autolysis. Yeast extract has long been in use as an additive to food products and today is used to increase the robust, broth-like flavor of soups, bouillon, and sauces. Several basic products based on various forms of yeasts have evolved as convenience broths and gravies. In addition to dry powders, yeast products in liquid, paste, or granular form have been produced to fill special production requirements.

As interest in yeast activities has grown, many properties of yeast extracts have been recognized. In addition to flavor enhancement, yeast extract has also exhibited emulsification properties. Many food products which benefit from the flavor enhancement of added yeast, also require emulsifiers to maintain their consistency and texture. Examples of such foods are those which are suspended in a water phase, contain fats or oils and which are not expected to separate, e.g., buttermilk or cream-based salad dressings and cheese sauce. Because some yeast extracts exhibit emulsification properties, no additional emulsifier need be present in the food containing said extract.

The flavor enhancing properties present in some yeast extracts make it possible for the yeast to modify flavor characteristics of foods, and intensify seasonings. These properties also reduce the need for sodium by altering the perceived flavor of sodium chloride in food systems so that the salt content can be reduced without a significant loss of salty taste. Yeast extracts also reduce if not eliminate the need for MSG by offering a safe, viable option to MSG use. Because flavor properties can be introduced into the substrate to produce yeast proteins that are essentially tailored to a specific flavor goal, flavor development for the future appears to be directed at the further exploitation of yeast and its properties.

It is therefore beneficial to identify and isolate novel extracts which have utility as flavor enhancers or as emulsifiers. Thus, providing such novel extracts from the yeast *Candida utilis* which act as either flavor enhancers or emulsifiers is a significant contribution to the art.

SUMMARY OF THE INVENTION

It is therefore an object of the present invention to provide a novel yeast extract which acts as a flavor enhancer and is derived from raw *Candida utilis* yeast cells.

It is another object of the present invention to provide a novel yeast extract which acts as an emulsifier and is derived from raw *Candida utilis* yeast cells.

It is yet another object of the present invention to provide a novel yeast extract which acts as a flavor enhancer and is derived from pasteurized, i.e. heated, *Candida utilis* yeast cells.

It is a further object of the present invention to provide a novel yeast extract which acts as an emulsifier and is derived from pasteurized *Candida utilis* yeast cells.

It is yet a further object to provide processes whereby the above novel yeast extracts are produced.

These and other objects of the present invention will become apparent upon inspection of the disclosure and the claims herein provided.

In accordance with the present invention, four novel yeast extracts from *Candida utilis* have been discovered. Two extracts are derived from raw *Candida utilis* and two extracts are derived from pasteurized *Candida utilis*. When raw *Candida utilis* is used, the process to produce a flavor enhancing extract and an emulsifying extract comprises: washing Candida yeast cells; rupturing the washed cells; centrifuging the ruptured cells to achieve a soluble portion and an insoluble portion; recovering the resulting soluble yeast extract which exhibits flavor enhancing properties; washing the insoluble portion; adjusting the pH of the washed cells from the insoluble portion; heating the pH adjusted cells; neutralizing the heated cells; separating the neutralized cells into a soluble portion and an insoluble portion; and recovering the resultant soluble yeast extract which exhibits emulsifying properties.

When pasteurized Candida is used, the process to produce a flavor enhancing extract and an emulsifying extract comprises: heating *Candida utilis* yeast cells; rupturing the heated cells; centrifuging the ruptured cells to achieve a soluble portion and an insoluble portion; recovering the resulting soluble yeast extract which exhibits flavor enhancing properties; heating the yeast extract at a temperature and for a time sufficient to precipitate bitter proteins; centrifuging to remove bitter precipitate; spray drying the remaining soluble portion which exhibits flavor enhancing properties which exhibits flavor enhancing properties; washing the insoluble portion; adjusting the pH of these washed cells; heating the pH adjusted cells; neutralizing the heated cells; separating the neutralized cells into a soluble portion and an insoluble portion and recovering the resultant soluble yeast extract which exhibits emulsifying properties.

DETAILED DESCRIPTION

As presently practiced, various types of fermentation processes and apparatuses known in the art can be utilized to produce a fermented suspension of yeast cells. A suitable yeast species has been deposited with the United States Department of Agriculture, Agriculture Research Service, Northern Regional Research Laboratories of Peoria, Ill., and is *Candida utilis* which has received the numerical designation NRRL Y-1082. The presently preferred fermentation process is described in Wegner, U.S. Pat. No. 4,617,274, issued on Oct. 14, 1986 and assigned to Phillips Petroleum Company.

When raw *Candida utilis* is employed, the cells of the fermentor effluent are first washed. This wash step may be carried out by separating the yeast cells from the spent medium employing any suitable means, for example, centrifugation. The cells are then resuspended in a wash medium of deionized water, distilled water or potable tap water. The yeast cells are separated from the suspension by any suitable means such as centrifugation to obtain the washed cells.

The washed cells are then ruptured by any of several known methods that are well known to those of skill in the art, such as high pressure homogenization, attrition in a sand or colloid mill, sonic disintegration, repeated freeze-thaw cycles, lytic enzymes, and the like. Mechanical methods are presently preferred. After the cells are ruptured, they are separated by any suitable separation means such as filtration or centrifugation to separate the cell debris (insoluble portion) from the soluble intracellular material (yeast extract). The soluble portion may be used as it is or further dried by any conventional drying means to obtain a dehydrated product. The resulting extract exhibits flavor enhancing properties.

The insoluble portion is then washed and reconstituted. The pH is then adjusted to be in the range of about 10 to about 11.5 with a preferred pH of about 11 with a basic solution such as ammonium hydroxide, sodium hydroxide, or potassium hydroxide.

The insoluble portion is then heated for a time period in the range of about 30 to about 120 minutes and at a temperature in the range of about 50° C. to about 70° C. A preferred heating continues for a time period of about 60 minutes and at a temperature of about 60° C.

The heated insoluble portion is then neutralized to a pH in the range of about 6 to about 8, with a preferred pH of 7. The neutralization is achieved by using an appropriate acid such as acetic acid, hydrochloric acid and other suitable acids. The suspension is then separated into a soluble portion and an insoluble portion using conventional methods such as centrifugation and the soluble yeast extract is recovered. The resulting yeast extract produced by the above process exhibits emulsifying properties and can be an effective emulsifier when used in food products.

According to the second embodiment of the present invention, a yeast extract useful as a flavor enhancer and a yeast extract useful as an emulsifier are derived from pasteurized, i.e. heated, *Candida utilis*.

The yeast cells are initially heated for a time period in the range of about 30 seconds to about 20 minutes and at a temperature of about 60° C. to about 100° C. A preferred heating continues for a time period of about 2 to about 5 minutes and at a temperature of about 75° C. to about 85° C.

The heated cells are then ruptured by any of several known methods, such as high pressure homogenization, attrition in a sand or colloid mill, sonic disintegration, repeated freeze-thaw cycles, lytic enzymes, and the like. Mechanical methods are presently preferred. Alternatively, the heated cells are dried by any conventional drying means such as spray-drying. The dried cells can be reconstituted with water and then subject to breakage. The rupture renders the intracellular material soluble. The soluble portion, the yeast extract, is then separated from the insoluble portion using conventional means well known to those skilled in the art, such as filtration or centrifugation.

The resulting extract exhibits flavor enhancing properties. An optional step which can be performed on this extract is that of debitterization. When heat is applied, bitter proteins will precipitate out. Therefore, debitterization is accomplished by heating the extract at a temperature and for a time period sufficient to precipitate the bitter proteins.

The insoluble portion which result from the initial heating and separating of pasteurized *Candida utilis* as discussed above, is the source of an emulsifying extract. This insoluble portion is treated in the same manner in which the insoluble portion derived from raw *Candida utilis* is treated. Namely, the insoluble portion is washed. These cells are thus reconstituted. The pH is then adjusted to be in the range of about 10 to about 11.5 with a preferred pH of about 11.

The cells are then heated for a time period in the range of about 30 to about 120 minutes and at a temperature in the range of about 50° C. to about 70° C. A preferred heating continues for a time period of about 60 minutes and at a temperature of about 60° C.

The heated cells are then neutralized to a pH in the range of about 6 to about 8, with a preferred pH of 7. The neutralization is achieved by using an acid such as acetic acid, hydrochloric acid and other suitable acids. The cells are then separated into a soluble portion and an insoluble portion using conventional methods of such centrifugation and the soluble yeast extract is recovered. The resulting yeast extract produced by the above process exhibits emulsifying properties and can be an effective emulsifier when used in food products.

EXAMPLES

The following examples have been provided merely to illustrate the practice of the invention and should not be read as to limit the scope of the invention or the appended claims in any way.

EXAMPLE I

In a continuous aerobic fermentation process, aqueous mineral salts medium and sucrose were fed to a fermentor inoculated with the yeast species *Candida utilis* NRRL Y-1082, at a rate such that sucrose was the growth-limiting nutrient. The fermentor was a 1,500-liter foam-filled fermentor with a liquid volume of about 650 liters, with automatic pH, temperature, and level control. Agitation was provided by three conventional paddle-type turbines driven at 800 rpm. The aeration rate was about 4 volumes of air per volume of ferment in the fermentor per minute. Anhydrous ammonia was added at a rate sufficient to maintain a pH of about 4 in the fermentation mixture.

The aqueous fermentation medium was prepared by mixing, with each liter of tap water, 11.9 mL of 75 weight percent $H_3PO_4$, 6.4 g of $K_2SO_4$, 5 g of $MgSO_4 \cdot 7H_2O$, 0.3 g of $CaSO_4 \cdot 2H_2O$, 1.8 g of 85 weight percent KOH, and 275 g of sucrose. The aqueous fermentation medium was fed into the fermentor at a rate of 120-140 liters per hour.

The trace mineral solution was prepared by mixing for each liter of solution 60 g of $FeSO_4 \cdot 7H_2O$, 1.5 g of $Na_2MoO_4 \cdot 2H_2O$, 0.2 g of $CoCl_2 \cdot 6H_2O$, 38 g of $ZnSO_4 \cdot 7H_2O$, 2.5 g of $MnSO_4 \cdot H_2O$, 5 g of $CuSO_4 \cdot 5H_2O$ and 4 mL of concentrated $H_2SO_4$ and sufficient deionized water to make 1 liter of solution. The trace mineral solution was fed into the fermentor at a rate of 480 to 560 mL per hour.

The fermentation was conducted at about 34° C. with an average retention time of about 5 to 6 hours. The cell density was typically about 140 grams of cells per liter of fermentor broth. The total solid contents of the fermentor was typically about 150 grams per liter.

The resulting yeast cells were separated from the fermentation broth by centrifugation, washed by suspension in water, followed by recentrifugation, dried via a spray drier and weighed. On a dried basis the yield of yeast cells typically was about 50 to 54 g per 100 g of sucrose.

EXAMPLE II

Fermentor effluent containing torula yeast (100 ml; about 150 grams per liter) obtained in Example I was washed twice with tap water. The washed yeast cells were mechanically broken using microfluidics/cell disruptor followed by centrifugation to separate the cell debris from the soluble fraction.

The soluble fraction (45 ml) separated from the cell debris after mechanical breaking of the cells was spray-dried with Buchii Benchtop spray dryer. The dried product can be used as salt-substitute. The sample was tested by making a 1% solution in $H_2O$ and evaluating the salty taste compared to a 1% solution of NaCl in $H_2O$. The test sample was found to have a similar salty flavor perception.

EXAMPLE III

Fermentor effluent containing torula yeast (100 ml about 150 grams per liter) obtained in Example I was washed twice with tap water. The washed yeast cells were mechanically broken using microfluidics/cell disruptor followed by centrifugation to separate the cell debris from the soluble fraction.

The cell debris was washed followed by reconstitution with 165 ml of water. The suspension was adjusted to pH 11 with NaOH and then heated for 1 hour at 60° C.

The heated suspension, while still warm, was neutralized using 1N HCl. Upon centrifugation, the cell debris was removed. The supernatant fraction was sprayed dried to be used as emulsifying agent.

A test sample of emulsifying agent was mixed with vinegar (⅛ cup), oil (soybean) (⅜ cup), and lemon juice (1.5 teaspoon) in a glass beaker by stirring slightly followed by vigorously shaking for 1 minute. A portion of the shaken mixture was poured into a clear container. The remainder of the sample (about half) was mixed with a Braun blender for 1 minute. This remaining mixture was poured into a second clear container. This was done to determine if physical handling made a difference in the emulsion, i.e. the holding ability of the supernatant, solids or yeast. The results showed that the sample obtained by the inventive method had the best emulsifying properties.

EXAMPLE IV

Fermentor effluent containing torula yeast (about 150 grams per liter) obtained in Example I was heated at 80° C. for 2-5 minutes followed by spray-drying. The spray-dried yeast product was rehydrated with water at a 9 parts water to 5 parts dried yeast. Half of this yeast was then mechanically broken. The other half (control) was not broken. Both samples were then centrifuged at 9000 rpm for 1.5 hours to separate the cell debris from the soluble fraction.

The soluble fraction was debitterized by heating to precipitate bitter proteins which were removed by centrifugation. The clear soluble portion was then spray-dried to be used as salt replacer with a low sodium mushroom soup at 0.75 weight percent of the soup. It was found that the fraction obtained from the broken cells (control) gave the most flavor enhancement and increased the saltiness among the fraction obtained from the unbroken cells and regularly spray-dried yeast.

EXAMPLE V

Fermentor effluent containing the torula yeast (about 150 grams per liter) obtained in Example I was heated at 80° C. for 2-5 minutes followed by spray-drying. The spray-dried yeast was then rehydrated as in Example IV. Again, half of this rehydrated yeast was mechanically broken and the other half (control) was not broken. Both samples were centrifuged as in Example IV.

The cell debris was washed followed by reconstitution with water. The suspension was adjusted to pH 11 and then heated at 60° C. for 1 hour. The heated suspension was neutralized followed by centrifugation to remove cell debris. The supernatant fraction was spray-dried to be used as emulsifier.

The test sample was mixed with vinegar (⅛ cup), oil (soybean) (⅜ cup), and lemon juice (1.5 teaspoon) in a glass beaker by stirring slightly followed by vigorously shaking for 1 minute. A portion of the shaken mixture was poured into a clear container. The remainder of the sample (about half) was mixed with a Braun blender for 1 minute. This remaining mixture was poured into a second clear container. This was done to determine if physical handling made a difference in the emulsion, i.e. the holding ability of the supernatant, solids or yeast. The results showed that the sample obtained by the inventive method had the best emulsifying properties.

That which is claimed is:

1. A process for the isolation of an extract from pasteurized *Candida utilis* cells which comprises:
    (a) heating *Candida utilis* yeast cells for a time period in the range of about 30 seconds to about 20 minutes and at a temperature in the range of about 75° C. to about 85° C.;
    (b) mechanically rupturing the heated cells;
    (c) separating the ruptured cells into a soluble portion and an insoluble portion; and
    (d) recovering the resulting soluble yeast extract.

2. The soluble yeast extract produced by the process of claim 1.

3. A process in accordance with claim 1 wherein the yeast cells are heated for a time period of about 2 to about 5 minutes.

4. A process in accordance with claim 1 further comprising:
    (a) heating the soluble yeast extract at a temperature and for a time sufficient to precipitate bitter proteins;
    (b) centrifuging to remove bitter precipitate; and
    (c) spray drying the remaining soluble portion.

5. The soluble portion produced by the process of claim 4.

* * * * *